United States Patent [19]
Ackerman et al.

[11] Patent Number: 5,814,166
[45] Date of Patent: Sep. 29, 1998

[54] PROCESS FOR HEAT TREATING AND TEMPERING SURGICAL NEEDLES

[75] Inventors: Douglas Warren Ackerman, Gainesville, Ga.; Timothy Sardelis, Somerset; William McJames, Belle Mead, both of N.J.

[73] Assignee: Ethicon, Inc., Somerville, N.J.

[21] Appl. No.: 748,875

[22] Filed: Nov. 14, 1996

[51] Int. Cl.[6] ................................................ C21D 9/26
[52] U.S. Cl. ........................... 148/606; 606/222; 163/5
[58] Field of Search ...................... 148/606; 606/222; 163/5

[56] References Cited

U.S. PATENT DOCUMENTS

| | | |
|---|---|---|
| 3,314,831 | 4/1967 | Hoenie et al. . |
| 5,330,441 | 7/1994 | Prasad et al. . |
| 5,358,577 | 10/1994 | Uehara et al. . |
| 5,411,613 | 5/1995 | Rizk et al. . |
| 5,533,982 | 7/1996 | Rizk et al. . |

*Primary Examiner*—Deborah Yee
*Attorney, Agent, or Firm*—Emil Richard Skula

[57] ABSTRACT

A continuous process for heat treating and cleaning and tempering martensitic stainless steel surgical needles is disclosed. The method comprises exposing the surgical needles to a partial vacuum at a temperature less than the heat treating temperature to remove volatile surface contaminant. Then the needles are heat treated in an argon gas environment at a pressure equal to or greater than 1.0 Torr. Next the temperature of the oven is lowered to temper the needles.

11 Claims, 2 Drawing Sheets

PROCESS FOR HEAT TREATING AND TEMPERING SURGICAL NEEDLES

TECHNICAL FIELD

The field of art to which this invention relates is heat treatment processes, in particular, heat treatment process for stainless steel surgical needles.

BACKGROUND OF THE INVENTION

Conventional surgical needles are typically made from stainless steels. The types of stainless steel which are used include Types 420SS, 455SS, 302SS, and certain proprietary alloys such as those disclosed in U.S. Pat. No. 5,000,912 which is incorporated by reference. Type 420SS stainless steel alloy is conventionally referred to as a martensitic stainless steel, while Type 302SS stainless steel alloy is referred to as an austenitic stainless steel. Type 455SS stainless steel alloys and the proprietary alloys referenced above are conventionally referred to as maraging or precipitation hardening stainless steel.

In a conventional surgical needle manufacturing process, wire is removed from a spool, straightened, and then cut into needle blanks. Optionally, the wire may be drawn to a finer diameter as it is removed from the spool. The needle blanks are then subjected to a variety of conventional forming, grinding and shaping processes to produce surgical needles having distal piercing points and proximal suture mounting sections (e.g., either channels or drilled holes). The needles may be tapered, and may have cutting edges. Conventional surgical needles are typically curved by bending the needle blanks, but may also have a straight configuration, or a configuration having a straight section and a curved section. Typically, portions of the surgical needles are flattened to assist in grasping the needles with conventional needle holding instruments.

It is known that stainless steel needles made from martensitic Type 420SS and maraging grades of stainless steel must be heat treated after the manufacturing process in order to improve the strength of the needle. For the Type 420SS grades, this heat treatment transforms the structure into martensite. While the transformation resulting from the heat treatment increases the mechanical strength of such martensitic stainless steel needles, it is accomplished with an accompanying decrease in ductility. In order to improve the ductility of heat treated surgical needles made from Type 420SS martensitic stainless steel, the needles are subsequently tempered.

The methods and processes for heat treating martensite Type 420SS grade stainless steel alloys are varied. The heat treatment can performed using a conventional process in a conventional continuous belt furnace where the surgical needles are fed through a hot zone at the reaction temperature. In this process temperature of the surgical needles increases to the reaction temperature in the hot zone. The needles are then passed into a cooler zone where the transformation takes place. This process typically takes place under a protective atmosphere of nitrogen, hydrogen or an inert gas.

Type 420SS stainless steel surgical needles may also be batch processed in a furnace. This process may also take place in a protective atmosphere of nitrogen, hydrogen or an inert gas.

For both of the previously-mentioned conventional processes, the needles are tempered after the initial heat treatment step in a separate furnace at a lower temperature. This can be done in air or under an atmosphere of nitrogen or inert gas.

In contrast, the heat treatment process (actually called aging in the metallurgical community) for maraging stainless steel surgical needles, such as Type 455SS stainless steel alloy, is a one step process. The maraging stainless steel surgical needles are heated to a temperature and held there for a specific amount of time. This aging can be done in air, under an atmosphere of nitrogen or inert gas or under vacuum.

Although the conventional processes for heat treating and tempering martensitic stainless steel surgical needles produce surgical needles having the desired ductility and strength, there are certain disadvantages associated with these processes. The disadvantages include the time and handling necessary to remove the needles from a heat treatment furnace, store the needles, and then temper them in a separate tempering oven. It is impractical to use the same equipment for both processes since the time needed to allow the heat treatment furnace to cool to the tempering temperature is excessive resulting in unacceptable downtime. An additional disadvantage of conventional processes is the necessity of removing any discoloration on the needles due to oxidation. This is especially true of surgical needles which have been tempered or aged in air, but even under nitrogen or inert gas there may be some oxidation present. This is usually due to the presence of contaminants on the needle or moisture in the gas. The conventional heat treating processes keep the surgical needles under vacuum during the entire cycle of heat treatment and tempering, thereby not allowing the contamination of the surgical needles during handling or the oxidation during tempering.

In addition, conventionally known and used heat treatment processes for heat treating martensitic stainless steel alloy surgical needles wherein stainless steels are held at elevated temperatures under vacuum for an extended time may cause the needles to exhibit a loss of the alloying element chromium. This typically has the effect of decreasing the corrosion resistance of the surgical needle in service.

Accordingly, there is a need in this art for improved heat treatment and tempering processes which overcome these and other disadvantages of conventional heat treatment and tempering precesses.

DISCLOSURE OF THE INVENTION

Therefore, there is an object of this invention to provide a novel process which allows martensitic surgical needles to be heat treated and tempered in a single continuous process.

It is an additional object of this invention to provide a heat treatment and tempering process which prevents the loss of alloying elements such as chromium when the surgical needles are exposed to a vacuum at high temperature for an extended period of time.

It is a further object of the present invention to provide a heat treatment and tempering process for surgical needles which also includes a cleaning step.

It is yet a further object of the present invention to provide a heat treatment and tempering process which minimizes or eliminates contamination of surgical needles during the process.

It is still yet a further object of the present invention to provide a heat treatment and tempering process which provides for more efficient heat treatment.

Accordingly, a process for heat treating and tempering martensitic stainless steel surgical needles is disclosed. The process consists of the steps of placing surgical needles into the chamber of a furnace. Next, the needles are exposed to a vacuum for a sufficient period of time at room temperature to effectively clean or remove volatile contaminants from the surfaces of the needles. Next, the needles are heated for a sufficient period of time at a sufficient temperature in a vacuum wherein the vacuum is maintained at a sufficient pressure to effectively remove additional contaminants. Then, the pressure is increased to about 1 Torr and heated to 1032° C. Next, the needles are held in the oven at a sufficient temperature for a sufficient period of time to effectively heat treat the needles by substantially transforming the structure of the needles to martensitic. After heat treatment, the needles are cooled by means of an inert gas back fill to a temperature less than the temperature at which the martensitic reaction takes place, for example, about 80° C. At or near 80° C. the surgical needles can be held under an inert atmosphere or a vacuum may be re-applied. The pressure of the back fill gas can vary from 760 to 4560 Torr (1 to 6 bar). The surgical needles are then heated to a sufficient temperature and maintained at that temperature for a period of time sufficient to effectively temper the surgical needles. After tempering, the needles are cooled and removed from the furnace.

The foregoing and other features and advantages of the present invention will become more apparent from the following description and accompanying drawings.

DESCRIPTION OF THE PREFERRED EMBODIMENTS

Figure 1:
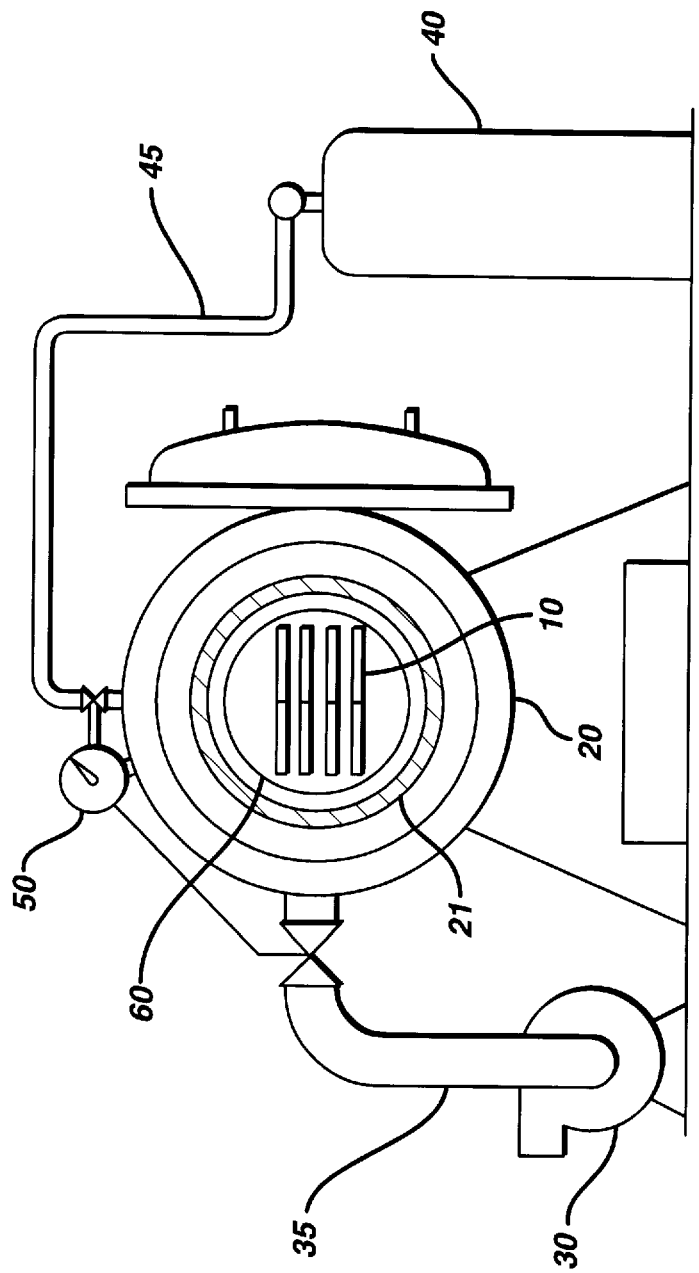
FIG. 1 is a schematic flow diagram of a heat treatment and tempering process of the present invention.

A schematic flow diagram of the process of the present invention is seen in FIG. 1. Untreated surgical needles 10 made from martensitic stainless steel alloy are placed into the chamber 21 of an oven 20. Heat treatment oven 20 may be any conventional oven capable of withstanding both pressure and vacuum. Typically oven 20 will be able to withstand an internal vacuum of at least $1 \times 10^{-4}$ Torr and an internal pressure of up to about 4560 Torr. It is preferred that oven 20 be heated with electric heating elements, although any conventional heat source or heating element may be used. After the needles 10 are secured within chamber 21 of oven 20, a vacuum is pulled upon the internal chamber 21 by vacuum pump 30 through pipe 35. The needles 10 are exposed to the vacuum for a sufficient period of time at room temperature to effectively clean the needles 10. Typically, the time will be about 1 minute to about 20 minutes, more typically about 2 minutes to about 10 minutes, preferably about 3 minutes to about 5 minutes. The vacuum pulled on cavity 21 will be sufficient to effectively volatize any volatile surface contamination on needles 10. Typically the vacuum will be about $2 \times 10^{-2}$ to about $1 \times 10^{-2}$ Torr, more typically about $2 \times 10^{-3}$ to about $1 \times 10^{-3}$ Torr, and preferably about $2 \times 10^{-4}$ to about $1 \times 10^{-4}$ Torr. Examples of volatile surface contaminants which can be removed during the cleaning process include conventional contaminants which result from needle manufacturing processes including, lubricating oils, greases and the like.

It is known in the art that contaminants, such as greases and oils, will volatize at different temperatures. By heating the surgical needles under vacuum, after initially cleaning at ambient room temperature, any volatile material not previously removed will be eliminated.

After the initial needle cleaning step, the temperature of the interior chamber 21 is increased at a constant rate to a sufficient level to effectively remove additional volatiles from the surface of the surgical needles while maintaining the vacuum level of the initial step. This temperature is below the reaction temperature for type 420SS stainless steel. During this step the temperature will typically range from about 625° C. to about 775° C., more typically about 650° C. to 750° C., and preferably about 675° C. to 725° C. The needles will be subjected to this temperature and vacuum for a sufficient amount of time to effectively clean the needles; typically about 1 minute to about 5 minutes, more typically about 2 minutes to about 4 minutes, and preferably about 2.5 minutes to about 3.5 minutes.

Then, once the desired temperature has been attained, a non-reactive or inert gas 40 is introduced into cavity 21 through pipe 45. The inert gases 40 which can be used include argon, nitrogen, and helium. It is particularly preferred to use argon. Typically, the camber 21 will be pressurized to a pressure of about 1 Torr to about 10 Torr, more typically about 1 Torr to about 5 Torr, and preferably about 1 Torr, maximum. The pressure in chamber 21 is maintained by conventional pressure regulator and controller 50.

After the chamber 21 is pressurized with gas 40, the heating elements 60 are energized to heat the gas 40 to a sufficient temperature for a sufficient amount of time to effectively heat treat the needles. Typically the heat treatment temperature will be about 1007° C. to about 1057° C., more typically about 1012° C. to about 1052° C., and preferably about 1017° C. to about 1047° C. The treatment time is typically about 1 to about 20 minutes, more typically about 2 to about 10 minutes, and preferably about 4 to about 6 minutes. The pressure is maintained at about 1.0 Torr maximum.

After the heat treatment phase is complete, the temperature in chamber 21 is decreased to a sufficient temperature for a sufficient period of time to allow the effective formation of the martensitic phase. This temperature is typically about 60° C. to about 140° C., more typically about 80° C. to about 120° C., and preferably about 60° C. to about 100° C. The time at which the surgical needles are held at this temperature is typically about 1 to about 20 minutes, more typically about 2 to about 10 minutes, and preferably about 4 to about 6 minutes. When the temperature of the chamber 21 is in the preferred range, the surgical needles can be held under the inert atmosphere or the vacuum may be re-applied. The inert gas pressure will be maintained with the pressure regulator 50 at 760 Torr, but may typically vary in the range of about 750 to 770 Torr. If a vacuum is applied, it will be about 2×10-2 to about 1×10-2 Torr, more typically about 2×10-3 to about 1 10 -3 Torr, and preferably about 2×10-4 to about 1 10-4 Torr.

Next, the temperature of the oven chamber 21 is increased to a tempering temperature. The needles are maintained in the oven at a sufficient tempering temperature for a sufficient period of time to effectively temper the needles. The tempering temperature will typically be about 200° C. to about 264° C., more typically about 202° C. to about 262° C., and preferably about 217° C. to about 247° C. The tempering time will typically be about 25 minutes to about 55 minutes, more typically about 30 minutes to about 50 minutes, and preferably about 35 minutes to about 45 minutes.

After the tempering step, the heat treated, tempered, martensitic stainless steel needles are cooled and removed from the oven. The needles have a clean surface substantially free from volatile contaminants and free from discoloration.

The following example is illustrative of the principles and practice of the present invention, although not limited thereto.

EXAMPLE 1

Figure 2:
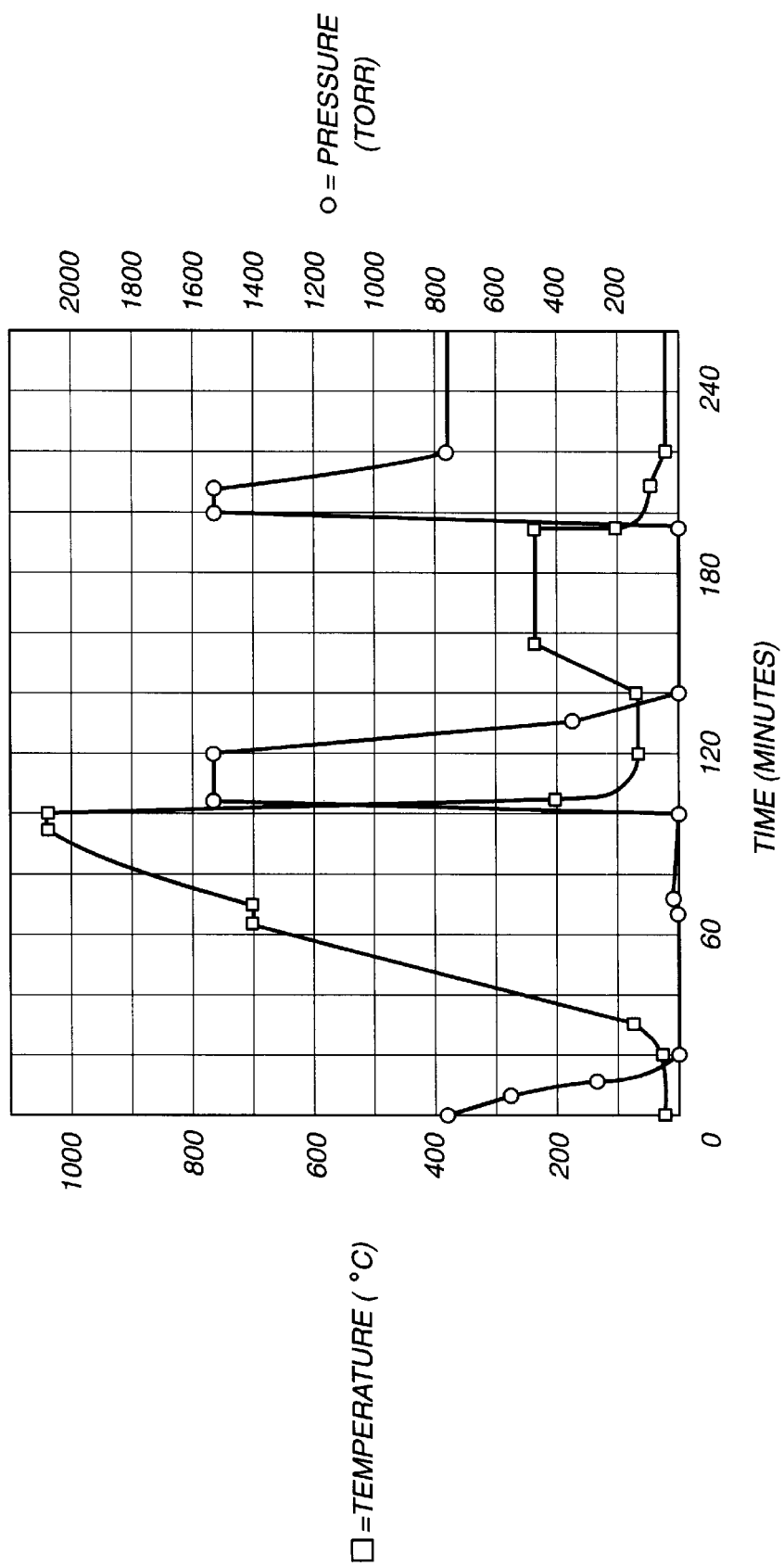
FIG. 2 is a graph of a preferred heat treatment and tempering cycle of the process of the present invention.

Surgical needles made from type 420SS stainless steel were heat treated using the process of the present invention as illustrated in the process diagram of FIG. 2. The needles were initially placed in a conventional oven capable of operating under both vacuum and pressure. The oven was equipped with electrical resistance heating elements. The oven chamber was evacuated to a vacuum of about $2 \times 10^{-4}$ Torr for about 1 minute at room temperature to remove volatile surface contaminants. Next, the oven temperature was increased to about 700° C. and maintained at that temperature for about 3 minutes to remove additional surface volatile contaminants. After the two cleaning steps are completed, a partial pressure of argon gas was introduced into the oven chamber. The partial pressure was maintained at 1 Torr maximum. The purpose of this partial pressure is to keep the alloying elements from being removed from the surface of the surgical needles at high temperature. When the chamber of the furnace reached an internal pressure of 1 Torr, the temperature was increased to the martensitic reaction temperature of 1032° C. and held at that temperature for 25 minutes to ensure thorough heating. After the 25 minutes had elapsed, argon gas was introduced into the chamber to lower the temperature at a pressure of 1520 Torr. Under this pressure, the temperature of the chamber decreased rapidly to about 80° C. When the surgical needles are at or near 80° C., the vacuum was re-applied to a level of 2×10 Torr and the chamber was heated to the tempering temperature of 232° C. and held there, under vacuum, for 40 minutes. After the tempering step was complete, the chamber was again cooled with argon gas at a pressure of 1520 Torr. When the surgical needles were at or near room temperature, 60° C., the pressure was reduced to atmospheric pressure and the surgical needles were removed from the furnace. The needles were then cooled and removed from the oven. The resulting ultimate tensile strength of the needles was measured at 260,000 psi and the bend strength was measured at 0.30 inch-pounds using conventional measuring apparatuses. The surgical needles had a 0.018 inch diameter. The needles exhibited good ductility.

As described above, an embodiment of a heat treatment process cycle of the present invention is illustrated in FIG. 2. The attached FIG. 2 shows the process parameters of pressure and temperature and time.

There are many advantages of heat treatment process of the present invention when compared to the prior art heat treatment and tempering processes. The advantages include better heat transfer, uniformity of heating, the ability to reduce oxide contamination on the surface of the needles, and the ability to more efficiently remove volatiles from the surfaces of the needles. It is believed that hardening under a pressure of at least 1 Torr provides for better or more efficient heat transfer.

In addition, the continuous nature of the process wherein heat treatment and tempering are combined, eliminates extra handling and possible resulting damage to the needles. In addition, the need for a separate tempering oven is eliminated. Furthermore, the needles come out of the process clean without the need for additional cleaning steps. In addition, it is believed that alloying elements are prevented from being removed from the exterior surfaces of the surgical needles.

Although this invention has been shown and described with respect to detailed embodiments thereof, it will understood by those skilled in the art that various changes in form and detail thereof may be made without departing from the spirit and scope of the claimed invention.

We claim:

1. A continuous process for heat treating and tempering stainless steel surgical needles, the process comprising initially placing a plurality of martensitic stainless steel surgical needles into an oven having an internal chamber, and exposing the needles to a sufficient vacuum at room temperature for a sufficient time to effectively remove surface volatile contaminants from the outer surfaces of the needles, said needles comprising a stainless steel containing alloy elements;

increasing the chamber temperature to a temperature less than or equal to 700° C. while maintaining a sufficient vacuum for a sufficient period of time to effectively remove higher temperature volatile surface contaminants from the outer surface of the needles while preventing the loss of alloy elements contained in the stainless steel;

then injecting an inert gas into the chamber at a pressure greater than or equal to 1 Torr, thereby cooling the needles and retaining the alloy elements;

heating the gas to a sufficient temperature and maintaining the gas at said temperature at a pressure of at least 1 Torr for a sufficient amount of time to effectively heat treat the needles;

lowering the temperature of the chamber to a sufficiently low temperature to allow the effective formation of the martensitic phase;

raising the temperature of the gas to a sufficient temperature and exposing the needles to a sufficient vacuum and maintaining said temperature and vacuum for a sufficient period of time to effectively temper the needles while maintaining the chamber pressure of at least 1.0 Torr.

2. The method of claim 1 wherein the vacuum in the initial cleaning step is about 2×10–4 Torr.

3. The method of claim 2 wherein the temperature in the second cleaning step is about 80° C. to about 700° C.

4. The method of claim 3 wherein the vacuum is about $2 \times 10^{-4}$ Torr.

5. The method of claim 1 wherein the pressure in the heat treatment step is about 1.0 Torr to about 20.0 Torr.

6. The method in claim 1 where the pressure of the inert gas introduced into the chamber for cooling can vary from 760 Torr to about 4560 Torr.

7. The method of claim 1 wherein the temperature in the heat treatment step is about 1007° C. to about 1057° C.

8. The method of claim 1 wherein the temperature in the tempering step is about 200° C. to about 264° C.

9. The method of claim 3 wherein the temperature in the second cleaning step is about 700° C.

10. The method of claim 5 wherein the temperature in the heat treatment step is about 1032° C.

11. The method of claim 1 wherein the pressure during the heat treatment step is about 1.0 Torr.

* * * * *